(12) United States Patent
Kay et al.

(10) Patent No.: US 8,129,510 B2
(45) Date of Patent: Mar. 6, 2012

(54) MINIGENE EXPRESSION CASSETTE

(75) Inventors: Mark Kay, Los Altos, CA (US);
Micheal Hebert, Sunnyvale, CA (US);
Petrus Wilhelmus Roelvink,
Gaithersburg, MD (US); David A. Suhy,
San Ramon, CA (US)

(73) Assignees: The Board of Trustees of the Leland Stanford Junior University, Palo Alto, CA (US); Benitec Biopharma Limited, Balmain, NSW (AU)

( * ) Notice: Subject to any disclaimer, the term of this patent is extended or adjusted under 35 U.S.C. 154(b) by 0 days.

(21) Appl. No.: 11/731,198

(22) Filed: Mar. 30, 2007

(65) Prior Publication Data
US 2007/0243168 A1 Oct. 18, 2007

Related U.S. Application Data

(60) Provisional application No. 60/787,459, filed on Mar. 30, 2006.

(51) Int. Cl.
*C07H 21/02* (2006.01)
*C07H 21/04* (2006.01)
*C12N 15/00* (2006.01)

(52) U.S. Cl. .................................. 536/23.1; 435/320.1

(58) Field of Classification Search .................. 536/23.1; 435/320.1
See application file for complete search history.

(56) References Cited

U.S. PATENT DOCUMENTS

| | | | |
|---|---|---|---|
| 6,808,905 B2 | 10/2004 | McArthur et al. | |
| 7,148,341 B2 | 12/2006 | Kleinschmidt et al. | |
| 2006/0189561 A1* | 8/2006 | Roelvink et al. | 514/44 |

FOREIGN PATENT DOCUMENTS

| WO | WO02/092134 A1 | 11/2002 |
|---|---|---|
| WO | WO2006/017325 A | 2/2006 |

OTHER PUBLICATIONS

Davidson, The genetics of TBP and TBP-related factors, Trends Biochem Sci. 28(7): 391-8, 2003.*
Kadonaga, The DPE, a core promoter element for transcription by RNA polymerase II, Exp Mol Med. 34(4):259-64, 2002.*
Kornberg, The molecular basis of eukaryotic transcription. Proc Natl Acad Sci U S A. 104(32): 12955-61, 2007.*
GenBank Accession No. AY661265, version AY661265.1 GI:50402339 (published on Jul. 25, 2004, two pages).*
Arruda et al., Regional intravascular delivery of AAV-2-F.IX to skeletal muscle achieves long-term correction of hemophilia B in a large animal model. Blood, 105(9):3458-64, 2005.*
New England Biolab 1995 Catalog (16 pages provided).*
Jaye et al., Isolation of a human anti-haemophilic factor IX cDNA clone using a unique 52-base synthetic oligonucleotide probe deduced from the amino acid sequence of bovine factor IX, Nucleic Acids Res. 11 (8), 2325-2335, 1983.*
Ehrhart et al., Somatic integration from an adenoviral hybrid vector into a hot spot in mouse liver results in persistent transgene expression levels in vivo, Mol Ther. 15(1):146-56, 2007.*
Kay et al. Evidence for gene transfer and expression of factor IX in haemophilia B patients treated with an AAV vector, Nat Genet. 24(3):257-61, 2000.*
U.S. Appl. No. 11/701,279, filed Jan. 31, 2007, Kay et al.
Gehrke, S. et al., *Gene*, 322:137 (2003).
McLellan, A.S., et al., *Am. J. Physiol. Cell Physiol*., 291(2):C300 (2006).
Nakai et al., *Journal of Virology*, 79(1):214-224 (2005).
Nathwani et al., *Blood*, 107(7):2653-2661 (2006).
Szymanski et al., *J. Gene Med*.,, 8(4):514 (2006).
Thomas et al., *Journal of Virology*, 78(6):3110-3122 (2004).
Xia, H. et al., *Nat. Biotechnol*., 20:1006 (2002).
Grimm, D. et al., *Journal of Virology*, 80(1):426-439 (2006).
Costa et al., *Molecular and Cell Biology*, 6(12):4697-4708 (2006).
Costa, Robert H. et al., Trascriptional Control of the Mouse Prealbumin (Transthyretin) Gene: Both Promoter Sequences and a Distinct Enhancer are Cell Specific:, *Molecular and Cellular Biology*, vol. 6, No. 12, pp. 4697-4708, (1986).

* cited by examiner

*Primary Examiner* — Wu-Cheng Winston Shen
(74) *Attorney, Agent, or Firm* — Judy M. Mohr; Susan J. Myers Fitch; King & Spalding LLP (57) ABSTRACT

Methods and compositions for expressing a gene or nucleotide sequence of interest are provided. The compositions include an expression cassette that includes a synthetic enhancer, a transthyretin promoter, and a nucleotide sequence operably under the control of the synthetic enhancer and the transthyretin promoter. The expression cassette may be used in an adeno-associated viral (AAV) vector, such as a self-complementary AAV vector.

9 Claims, 4 Drawing Sheets

MINIGENE EXPRESSION CASSETTE

CROSS-REFERENCE TO RELATED APPLICATIONS

This application claims the benefit of U.S. Provisional Application No. 60/787,459, filed Mar. 30, 2006, incorporated herein by reference in its entirety.

FEDERALLY-SPONSORED RESEARCH OR DEVELOPMENT

This invention was made with Government support under contracts HL064274 & HL066948 awarded by the National Institutes of Health. The Government has certain rights in this invention.

STATEMENT REGARDING GOVERNMENT INTEREST

This work was supported in part by the National Institutes of Health (NIH) Grant number HL 64274. Accordingly, the United States government may have certain rights.

TECHNICAL FIELD

The subject matter described herein relates to expression cassettes. More particularly, liver-specific expression cassettes are described.

BACKGROUND

Recombinant gene therapy techniques have been developed and evaluated in preclinical and clinical tests over the last fifteen years. Gene therapy techniques are particularly promising for treating diseases or deficiencies that are caused by a deficiency or abnormality in the expression of a particular gene in specific cell or tissue types because a gene of interest can be placed under the control of a cell-specific or tissue-specific promoter to achieve location-specific expression of that gene. In particular, there has been significant interest in developing gene therapy techniques to treat liver-specific diseases or deficiencies.

Multiple recombinant gene transfer vectors based on different types of viruses have been developed and tested in clinical trials in recent years. Gene transfer vectors based on adeno-associated virus (AAV) have become favored vectors because of characteristics such as an ability to (i) transduce different types of dividing and non-dividing cells of different tissues, and (ii) establish stable, long-term transgene expression. While vectors based on other viruses, such as adenoviruses and retroviruses, also posses such desirable characteristics, the use of other vectors has been associated with toxicity of some human diseases. These side effects have not been detected with gene transfer vectors based on AAV. Additionally, the technology to produce and purify AAV-based vectors without undue effort has been developed.

AAV-based vectors have provided encouraging results for providing a method of liver-specific gene expression. For example, clinical trials showed that a recombinant AAV vector containing a factor IX (FIX) sequence was able to produce a therapeutic circulating level of FIX protein from hepatocytes in hemophilia B patients. A deficiency of FIX, which is a coagulation factor normally produced by the liver, is the cause of hemophilia B. Hemophilia B is an ideal disease target for gene therapy because it is due to a single gene mutation and because a small increase in the circulating levels of FIX is sufficient to measurably reduce the symptoms of hemophilia B. However, it was observed in the clinical trials described above that the circulating level of FIX protein dropped below therapeutic levels after several weeks (Wang, L. et al., Curr. Gene Ther. 5:349-360 (2005); High, K. A., Semin. Thromb. Hemost., 30:257-267 (2004)). It is believed that the high doses of the recombinant AAV vector that were used triggered an immune response against the transduced hepatocytes.

Thus, there remains a need for providing liver-specific expression of a gene. In particular, there is a need for liver-specific expression constructs that provide robust expression levels from viral vectors that do not trigger an inactivating immune response.

The foregoing examples of the related art and limitations related therewith are intended to be illustrative and not exclusive. Other limitations of the related art will become apparent to those of skill in the art upon a reading of the specification and a study of the drawings.

BRIEF SUMMARY

In one aspect, compositions for expressing a gene or nucleotide sequence of interest in the liver are provided. The compositions are comprised of an expression cassette comprising a synthetic enhancer, a transthyretin promoter, and a nucleotide sequence operably under the control of the synthetic enhancer, and the transthyretin promoter.

In one embodiment, the synthetic enhancer and the transthyretin promoter have a sequence selected from the group consisting of sequences having at least about 80% sequence identity to SEQ ID NO:3 and SEQ ID NO: 3.

In another embodiment, the synthetic enhancer and the transthyretin promoter have a sequence selected from the group consisting of sequences having at least about 80% sequence identity to SEQ ID NO:7 and SEQ ID NO:7.

In another embodiment, the nucleotide sequence that is operably under the control of the synthetic enhancer and the transthyretin promoter is a factor IX sequence.

In another aspect, vectors comprising a composition as described above are provided.

In various embodiments, the vector is an AAV vector, such as a self-complementary AAV vector.

In another embodiment, the vector is comprised of three plasmids: a first plasmid comprising an expression cassette comprising a synthetic enhancer, a transthyretin promoter, and a nucleotide sequence operably under the control of the synthetic enhancer and the transthyretin promoter; a second plasmid comprising adenoviral helper genes; and a third plasmid comprising AAV replication and capsid genes.

In one embodiment, the synthetic enhancer and the transthyretin promoter have a sequence selected from the group consisting of sequences having at least about 80% sequence identity to SEQ ID NO:3 and SEQ ID NO: 3, the nucleotide sequence that is operably under the control of the synthetic enhancer and the transthyretin promoter is a factor IX sequence, and the capsid gene is an AAV-2 or an AAV-8 capsid gene.

In another embodiment, the synthetic enhancer and the transthyretin promoter have a sequence selected from the group consisting of sequences having at least about 80% sequence identity to SEQ ID NO:7 and SEQ ID NO: 7, the nucleotide sequence that is operably under the control of the synthetic enhancer and the transthyretin promoter is a factor IX sequence, and the capsid gene is an AAV-2 or an AAV-8 capsid gene.

In another aspect, methods of expressing a nucleotide of interest in a mammalian liver by delivering to the liver an expression cassette comprising a synthetic enhancer, a transthyretin promoter, and the nucleotide sequence operably under the control of the synthetic enhancer and the transthyretin promoter.

In one embodiment, expression of a nucleotide of interest is for use in a treating a disease or disorder by expressing a protein encoded by the nucleotide of interest in a therapeutically effective amount.

In one embodiment, the method comprises delivery of a vector for expression of factor IX (FIX) for treatment of hemophilia B.

In addition to the exemplary aspects and embodiments described above, further aspects and embodiments will become apparent by reference to the drawings and by study of the following descriptions.

BRIEF DESCRIPTION OF THE SEQUENCES

SEQ ID NO:1 is a nucleotide sequence of a synthetic enhancer.

SEQ ID NO:2 is a nucleotide sequence of a transthyretin promoter.

SEQ ID NO:3 is an example of a sequence including a synthetic enhancer (SynEnh) sequence followed by a transthyretin sequence with several nucleotides between the two sequences.

SEQ ID NO:4 is a nucleotide sequence of a portion of the human FIX gene with a 0.3 kb mini-intron and a synthetic polyadenylation signal of about 70 bp.

SEQ ID NO:5 is a nucleotide sequence that includes a portion of the canine FIX gene with a 0.3 kb mini-intron (which was reduced from the 1.4 kb intron A in the canine FIX gene) and a synthetic polyadenylation signal of about 70 bp.

Figure 3:
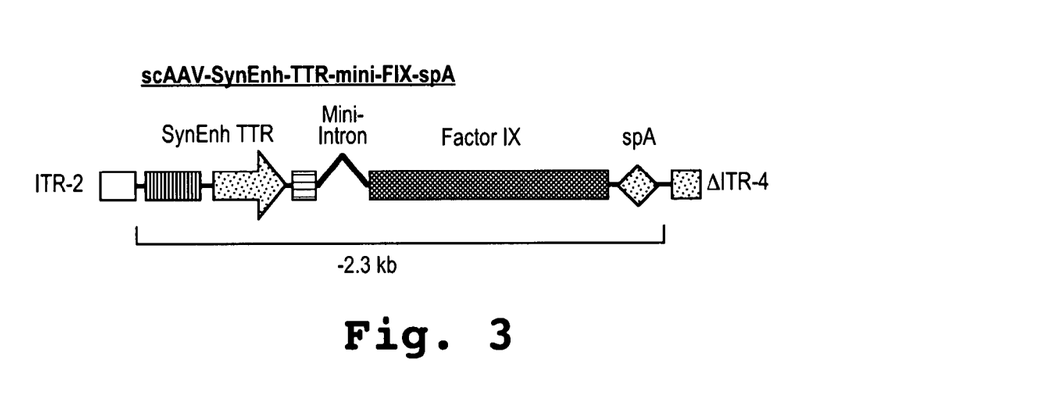
FIG. 3 is schematic diagram of a construct for a self-complementary AAV (scAAV) vector plasmid.

SEQ ID NO:6 is the nucleotide sequence of an expression cassette as depicted in FIG. 3 and comprised of an enhancer/promoter of SEQ ID NO:7, a FIX gene and intron of SEQ ID NO:9, and a poly-A signal of SEQ ID NO:10.

SEQ ID NO:8 is an intron sequence associated with the expression cassette of SEQ ID NO:6, and more particularly with the FIX gene of SEQ ID NO:9.

DETAILED DESCRIPTION

I. Definitions

The practice of the subject matter described herein will employ, unless otherwise indicated, conventional techniques of molecular biology, microbiology, cell biology and recombinant DNA, which are within the skill of the art. See, e.g., Sambrook, Fritsch, and Maniatis, MOLECULAR CLONING: A LABORATORY MANUAL, 2nd edition (1989); CURRENT PROTOCOLS IN MOLECULAR BIOLOGY, (F. M. Ausubel et al. eds., 1987); the series METHODS IN ENZYMOLOGY (Academic Press, Inc.); PCR 2: A PRACTICAL APPROACH (M. J. McPherson, B. D. Hames and G. R. Taylor eds., 1995) and ANIMAL CELL CULTURE (R. I. Freshney. Ed., 1987).

As used in this specification and the appended claims, the singular forms "a," "an" and "the" include plural references unless the content clearly dictates otherwise.

A polynucleotide is typically composed of a specific sequence of four nucleotide bases: adenine (A); cytosine (C); guanine (G); and thymine (T) (uracil (U) for thymine (T) when the polynucleotide is RNA). Thus, the term polynucleotide sequence is the alphabetical representation of a polynucleotide molecule. This alphabetical representation can be input into databases in a computer having a central processing unit and used for bioinformatics applications such as functional genomics and homology searching.

An "isolated polynucleotide" molecule is a nucleic acid molecule separate and discrete from the whole organism with which the molecule is found in nature; or a nucleic acid molecule devoid, in whole or part, of sequences normally associated with it in nature; or a sequence, as it exists in nature, but having heterologous sequences in association therewith.

Techniques for determining nucleic acid and amino acid "sequence identity" also are known in the art. Typically, such techniques include determining the nucleotide sequence of the mRNA for a gene and/or determining the amino acid sequence encoded thereby, and comparing these sequences to a second nucleotide or amino acid sequence. In general, "identity" refers to an exact nucleotide-to-nucleotide or amino acid-to-amino acid correspondence of two polynucleotides or polypeptide sequences, respectively. Two or more sequences (polynucleotide or amino acid) can be compared by determining their "percent identity." The percent identity of two sequences, whether nucleic acid or amino acid sequences, is the number of exact matches between two aligned sequences divided by the length of the shorter sequences and multiplied by 100. Percent identity may also be determined, for example, by comparing sequence information using the advanced BLAST computer program, including version 2.2.9, available from the National Institutes of Health. The BLAST program is based on the alignment method of Karlin and Altschul. *Proc. Natl. Acad. Sci. USA* 87:2264-2268 (1990) and as discussed in Altschul, et al., *J. Mol. Biol.* 215:403-410 (1990); Karlin And Altschul, *Proc. Natl. Acad. Sci. USA* 90:5873-5877 (1993); and Altschul et al., *Nucleic Acids Res.* 25:3389-3402 (1997). Briefly, the BLAST program defines identity as the number of identical aligned symbols (i.e., nucleotides or amino acids), divided by the total number of symbols in the shorter of the two sequences. The program may be used to determine percent identity over the entire length of the proteins being compared. Default parameters are provided to optimize searches with short query sequences in, for example, blastp with the program. The program also allows use of an SEG filter to mask-off segments of the query sequences as determined by the SEG program of Wootton and Federhen, *Computers and Chemistry* 17:149-163 (1993). Ranges of desired degrees of sequence identity are approximately 80% to 100% and integer values therebetween. Typically, the percent identities between a disclosed sequence and a claimed sequences are at least 80%, at least 85%, at least 90%, at least 95%, or at least 98%.

Alternatively, the degree of sequence similarity between polynucleotides can be determined by hybridization of polynucleotides under conditions that form stable duplexes between homologous regions, followed by digestion with single-stranded-specific nuclease(s), and size determination of the digested fragments. Two DNA, or two polypeptide sequences are "substantially homologous" to each other when the sequences exhibit at least about 80-85%, preferably 85-90%, more preferably 90-95%, and most preferably 98-100% sequence identity to the reference sequence over a defined length of the molecules, as determined using the methods above. As used herein, substantially homologous also refers to sequences showing complete identity to the specified DNA or polypeptide sequence. DNA sequences that are substantially homologous can be identified in a Southern hybridization experiment under, for example, stringent conditions, as defined for that particular system. Defining appropriate hybridization conditions is within the skill of the art. See, e.g., Sambrook et al., supra; DNA Cloning, supra; Nucleic Acid Hybridization, supra.

II. Expression Cassettes and Vectors

In a first aspect, an expression cassette comprising a gene or nucleotide sequence of interest is provided. In another aspect, vectors comprising the expression cassette, for expressing the gene or nucleotide sequence of interest in a tissue, and in particular in the liver, and particularly in mammalian livers, are provided. The expression cassettes and exemplary vectors will now be described.

Figure 1A:
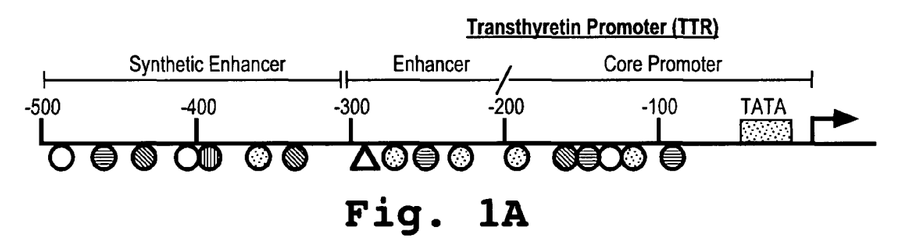
FIGS. 1A-1B are schematic diagrams of constructs including a synthetic enhancer fused to a transthyretin (TTR) promoter.
Figure 1B:
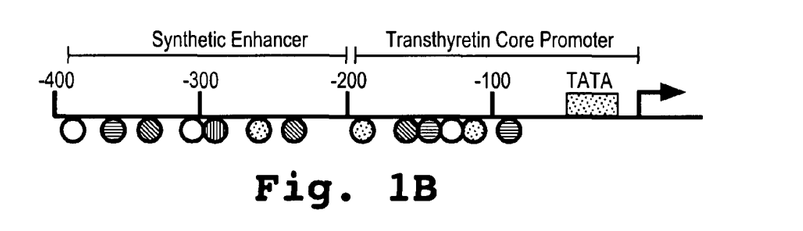

In one embodiment, the expression cassette comprises a synthetic enhancer (SynEnh), a transthyretin promoter (TTR), and a nucleotide sequence operably under the control of the synthetic enhancer and the transthyretin promoter. Exemplary constructs are shown in FIGS. 1A-1B, where a synthetic enhancer is fused to a transthyretin promoter (SynEnh-TTR). The synthetic enhancer sequence comprises a series of binding sites for activator proteins that regulate the expression of the nucleotide sequence under the control of the synthetic enhancer and the transthyretin promoter. The binding sites include, for example, binding sites for hepatocyte nuclear factors 1, 3, 4, and 6 (HNF-1, HNF-3, HNF-4, and HNF-6) and the liver specific enhancer binding protein (C/EBP).

A synthetic enhancer sequence that may be used is shown in SEQ ID NO: 1, and it is contemplated that enhancer sequences that hybridize to SEQ ID NO:1 under stringent conditions are also suitable for use in the expression cassette. Other suitable synthetic enhancer sequences are known in the art, and include but are not limited to those disclosed by Szymanski, P. et al., *J. Gene Med.,* 8(4):514 (2006); Gehrke, S. et al., *Gene,* 322:137 (2003); and McLellan, A. S., et al., *Am. J. Physiol. Cell Physiol.,* 291(2):C300 (2006)).

The full length TTR promoter normally controls expression of the serum thyroxine-binding protein, which is made by hepatocytes and by the choroid plexus epithelium in adults. In one embodiment, a preferred TTR promoter is a TTR promoter in which the region which controls choroids plexus expression is deleted. The preferred TTR promoter described herein retains the regions which drive liver-specific expression. With continuing reference to FIG. 1A, a preferred TTR promoter includes a core promoter region and an endogenous enhancer region. A preferred TTR promoter also includes binding sites for hepatocyte nuclear factors 1, 3, 4, and 6 (HNF-1, HNF-3, HNF-4, and HNF-6), the liver specific enhancer binding protein (C/EBP), and activating protein 1 (AP-1). A sequence of a preferred TTR promoter is shown in SEQ ID NO: 2, and it is contemplated that sequences that hybridize to SEQ ID NO:2 under stringent conditions are also suitable for use in the expression cassette.

FIG. 1B shows another preferred TTR promoter, wherein an endogenous TTR enhancer portion of the promoter has been removed. This preferred TTR promoter is identified herein as SEQ ID NO:7.

The SynEnh and TTR sequences in the expression cassette may be directly adjacent or separated by a short region of nucleotides. The short region of nucleotides may include one or more restriction enzyme sites. An example of a sequence including a SynEnh sequence followed by a TTR sequence with several nucleotides between the two sequences is shown in SEQ ID NO: 3.

As noted above, a nucleotide sequence is operably linked to the SynEnh-TTR sequence. A gene is "operably linked" to another nucleotide sequence when it is placed in a functional relationship with another nucleotide sequence. For example, if a coding sequence is operably linked to a promoter sequence, this generally means that the promoter may promote transcription of the coding sequence. Operably linked means that the DNA sequences being linked are typically contiguous and, where necessary to join two protein coding regions, contiguous and in reading frame. However, since enhancers may function when separated from the promoter by several kilobases and intronic sequences may be of variable length, some nucleotide sequences may be operably linked but not contiguous. Additionally, as defined herein, a nucleotide sequence is intended to refer to a natural or synthetic linear and sequential array of nucleotides and/or nucleosides, and derivatives thereof. The terms "encoding" and "coding" refer to the process by which a nucleotide sequence, through the mechanisms of transcription and translation, provides the information to a cell from which a series of amino acids can be assembled into a specific amino acid sequence to produce a polypeptide.

The nucleotide sequence that is operably under the control of the synthetic enhancer and the transthyretin promoter may encode a gene or at least a part of a gene of interest. The gene may be an endogenous or viral gene, and may be associated with a disease or pathology.

In one aspect, the nucleotide sequence that is operably under the control of the synthetic enhancer and the transthyretin promoter encodes a gene or a part of a gene whose expression is desired in the liver. The gene's expression in the liver may be desired in order to produce a protein encoded by the gene that is either missing or abnormal in the subject liver. The gene may be a gene that is normally expressed in the liver or a gene that is not normally expressed in the liver.

In one embodiment, the nucleotide sequence that is operably under the control of the synthetic enhancer and the transthyretin promoter is a factor IX (FIX) sequence. The FIX sequence may be a human sequence or a non-human sequence, e.g., a non-human mammalian sequence. In one embodiment, the FIX sequence is SEQ ID NO: 4, which is a sequence that includes a portion of the human FIX gene with a 0.3 kb mini-intron and a synthetic polyadenylation signal of about 70 bp (Xia, H. et al., *Nat Biotechnol.*, 20:1006 (2002)).

In another embodiment, the FIX sequence is SEQ ID NO: 5, which is a sequence that includes a portion of the canine FIX gene with a 0.3 kb mini-intron (which was reduced from the 1.4 kb intron A in the canine FIX gene) and a synthetic polyadenylation signal of about 70 bp.

In another embodiment, the FIX sequence is SEQ ID NO:9, wherein the intron sequence has been shortened by about 200 bp. The shortened intron is identified herein as SEQ ID NO:8.

While preferred sequences are described for the synthetic enhancer, transthyretin promoter, and nucleotide sequence that is operably under the control of the synthetic enhancer and the transthyretin promoter are provided above, it is recognized that the sequences may be varied yet retain similar function. In particular, sequences that hybridize under stringent conditions to any of the nucleotide sequences described herein are contemplated for use in the expression cassettes, vectors, and methods of use.

A study was conducted to evaluate the activity and specificity of an expression cassette comprising the sequence of SEQ ID NO: 3, which comprises SynEnh and TTR sequences. As described in Example 1, a first plasmid was constructed in which the Renilla luciferase gene was placed under the control of the synthetic enhancer and the transthyretin promoter. A second plasmid was constructed in which the Renilla luciferase gene was placed under the control of a wildtype TTR promoter. Huh-7 and HEK293 cells were transiently transfected with the plasmids, along with a control vector expressing the firefly luciferase gene. Following incubation at standard tissue culture conditions for 36 hours, the levels of Renilla and firefly luciferase were measured. Results are shown in Table 1.

TABLE 1

Promoter Activity in Kidney and Hepatoma Cell Lines.

| Cell Line | Enhancer-Promoter | Relative Luciferase Levels Renilla/Firefly)[1] | Fold Increase with Synthetic Enhancer | Fold Increase for Liver Specific Expression |
|---|---|---|---|---|
| HuH-7 (liver) | TTR | 2.25 (±0.4) | — | 2 |
|  | SynEnh-TTR | 27 (±2.3) | 12 | 42 |
| HEK293 (Kidney) | TTR | 1 (±0.1) | — | — |
|  | SynEnh-TTR | 0.63 (±0.04) | 0.61 | — |

[1]Relative luciferase levels were normalized to the TTR expression in HEK293 cells. Standard deviations are indicated in parentheses.

As shown in Table 1, the plasmid with the SynEnh-TTR expression cassette produced a 42 fold higher level of liver specific luciferase expression than the plasmid with the wildtype TTR promoter.

In another study, described in Example 2, the activity of an expression cassette comprising the SynEnh-TTR construct was evaluated in vivo. Plasmids containing an expression cassette with the human or canine FIX (SEQ ID NO: 4 and SEQ ID NO: 5, respectively) under the control of SynEnh-TTR (SEQ ID NO: 3) were prepared. In addition, plasmids containing the human or canine FIX sequences (SEQ ID NO: 4 and SEQ ID NO: 5, respectively) under the control of the apolipoprotein E hepatic control region (ApoE-HCR) and the human α1-antitrypsin promoter (hAAT) were prepared. The four plasmids were injected into mice and circulating FIX levels were measured three days post-injection. The results are shown in FIG. 2.

Figure 2:
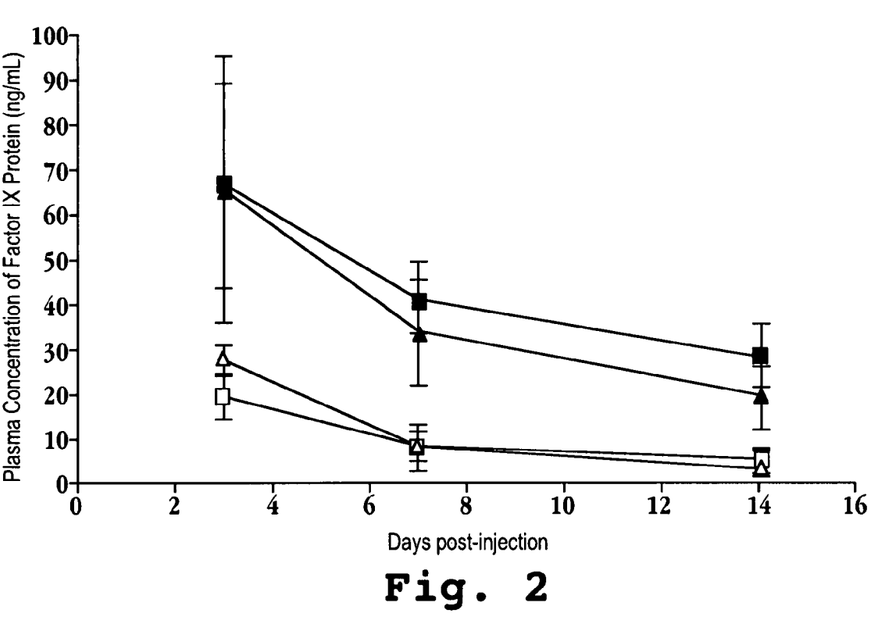
FIG. 2 is a graph showing the plasma concentration of factor IX (FIX) protein, in ng/mL, as a function of days post-injection into mice, of plasmids containing expression cassettes where human and canine FIX were under control of a synthetic enhancer and transthyretin promoter (SynEnh-TTR, SEQ ID NO:3) construct (open squares and triangles) or under control ApoE-HCR and the human a1-antitrypsin promoter (hAAT) (closed squares and triangles)

As seen in FIG. 2, while the expression cassettes that included FIX under the control of SynEnh-TTR (open triangles and squares) produced approximately 2.5 fold less FIX than the plasmids containing FIX under the control of the apolipoprotein E hepatic control region (ApoE-HCR) and the human α1-antitrypsin promoter (hAAT, closed triangles and squares), this difference is not significant in view of the fact that the SynEnh-TTR is about 1.5 kb smaller than the other cassettes. Also, the expression of FIX from a cassette comprising the SynEnh-TTR construct can be increased approximately 8-20 fold relative to the expression of FIX under the control of the apolipoprotein E hepatic control region (ApoE-HCR) and the human α1-antitrypsin promoter (hAAT) when inserted into a cassette comprising the SynEnh-TTR construct into a self-complementary AAV vector (scAAV), which is typically 20 to 50 fold more efficacious than a single-stranded AAV vector (2.5 fold less×20 to 50 fold more efficient=8 to 20 fold more efficient). Self-complementary AAV vectors are described in U.S. application Ser. No. 11/701,279 filed Jan. 31, 2007, which is incorporated by reference herein.

An example of a scAAV vector is diagramed in FIG. 3. scAAV vectors contain a linear DNA sequence that includes a transgene and an inverted repeat of the transgene. Because of the presence of both the transgene and the inverted repeat of the transgene, scAAV vectors fold back on themselves upon entering the nucleus to quickly form the double stranded DNA that is either formed into circular episomal DNA or integrated in the host genome to provide transgene expression. The time required for "conventional" single-stranded AAV vectors to be converted into double stranded DNA by either replication or positive and negative strand annealing is a rate limiting step that may hinder the expression of transgenes from single-stranded AAV vectors.

The construct shown in FIG. 3 includes the expression cassette comprising the human or canine FIX (SEQ ID NOs:4 and 5, respectively) under the control of SynEnh-TTR (SEQ ID NO: 3), as described above. The expression cassette is located between an inverted terminal repeat (ITR) of AAV serotype 2 (AAV-2) and an ITR of AAV serotype 4 (AAV-4). There is approximately 50% sequence identity between the ITRs of AAV-2 and AAV-4. The terminal resolution site (trs) of the ITR of AAV-4 used herein is deleted, and thus the right ITR is labeled as ΔITR-4. The use of different ITRs helps prevent recombination repair of the trs. This particular combination of ITRs results in more efficient replication, more infectious particles, and higher particle titers than constructs including both AAV-2 ITRs. A skilled artisan will appreciate that other combinations of ITRs may be used, such as ITRs from other AAV serotypes.

The construct shown in FIG. 3 was placed in a pSC-U6 plasmid, which is a pBluescript ks II (+) based vector, to provide an AAV vector plasmid. The AAV vector plasmid included an inverted repeat of the region of the construct shown in FIG. 3 that is between the ITRs, and thus is a scAAV vector plasmid.

The scAAV vector plasmid described above is preferably used in combination with a second plasmid comprising adenoviral helper genes and a third plasmid comprising AAV replication (rep) and capsid (cap) genes to triple transfect HEK293 cells, as previously described (Nakai, et al., *Journal of Virology*, 79:214-24 (2005); Thomas et al., *Journal of Virology*, 78:3110-22 (2004)). The AAV rep and cap genes are the two AAV genes that encode AAV replication and capsid proteins, respectively. As defined herein, the scAAV vector plasmid in combination with a plasmid providing adenoviral helper genes and a plasmid comprising AAV rep and cap genes is an AAV vector, more specifically, a scAAV vector, that can be used to provide recombinant AAV in cells that are triple transfected with the three plasmids. Also, plasmids encoding scAAV vector genomes including either the human or canine FIX expression cassettes provided herein can be injected into mice by hydrodynamic tail vein injection to observe the FIX protein levels obtained from the vectors.

Preferably, the AAV cap genes provide an AAV-2 or AAV-8 capsid, more preferably, an AAV-8 capsid. It has been observed previously that AAV-8 vectors are more efficient at gene transfer in vivo than AAV-2 vectors. AAV-8 vectors appear to be equally efficient at liver transduction if administered by peripheral IV or hepatic vessel infusion. Also, as AAV-8 has a non-human origin, it is unlikely that pre-existing anti-AAV-8 antibodies will limit transduction in human patients treated with AAV-8 vectors.

The expression cassettes and vectors described herein provide several advantages over prior expression cassettes and vectors. For example, the synthetic enhancer and transthyretin promoter provide a short control sequence that is able to drive robust, liver-specific expression of a gene. The shortness of the synthetic enhancer and transthyretin promoter allows for the use of longer genes or gene fragments in a vector including the synthetic enhancer and transthyretin promoter, as well as the use of the expression cassettes in double stranded AAV vectors, such as self-complementary AAV vectors, that have been observed to be from 20 to 50 times more efficient than single-stranded vectors, but typically can only accept 2.3 to 2.4 kb of exogenous nucleotide sequence. Also, a lower vector dosage is required to achieve a therapeutic result because of the efficiency of the expression cassette itself in combination with the efficiency of self complementary AAV vectors. The use of lower vector dosage reduces the probability of transduced cells being recognized and destroyed by an immune response, such as a cytotoxic T lymphocyte (CTL) response that has been observed in other clinical trials.

A scAAV expression cassette as depicted in FIG. 3 was constructed and tested in vivo for expression (data not shown). The expression cassette (SEQ ID NO:6) was comprised of a synthetic enhancer and TTR promoter (SEQ ID NO:7), a factor IX mini-gene (SEQ ID NO:9) including a mini-intron (SEQ ID NO:8) and a synthetic polyadenylation signal (SEQ ID NO:10). This scAAV construct was administered in vivo, as will be described below.

III. Methods of Use

In another aspect, methods of expressing a gene or nucleotide of interest are provided. In a preferred embodiment, a nucleotide sequence of interest is expressed in a selected tissue for treatment of a genetic disorder. For example, hemophilia B is a genetic disorder caused by a deficiency in coagulation factor IX (FIX) normally produced in the liver, and manifests as unpredictable, recurrent, and spontaneous bleeding in soft tissues and/or major joints. This recurrent bleeding can lead to crippling joint abnormalities in the most severely affected individuals.

Accordingly, in one embodiment, a vector containing an expression cassette a synthetic enhancer, a transthyretin promoter, and a nucleotide sequence operably under the control of the synthetic enhancer and the transthyretin promoter, wherein the synthetic enhancer and the transthyretin promoter comprise the sequence of SEQ ID NO: 3.

In another embodiment, a self-complementary AAV vector containing an expression cassette that is flanked by AAV inverted terminal repeats (ITR) of serotype 2 and 4 (~50% sequence identity), where the trs of the right AAV4 ITR is deleted (ITR-4).

For treatment of hemophilia B, the vector contains a nucleotide sequence encoding for a factor IX protein. Expression of the protein after introduction of the vector to the subject is effective to increase the circulating levels of the protein in the blood.

The vector is introduced to the mammal, typically by injection, intravenously, subcutaneously, parenterally, or the like, in an amount to provide a therapeutically effective amount of the protein.

Figure 4:
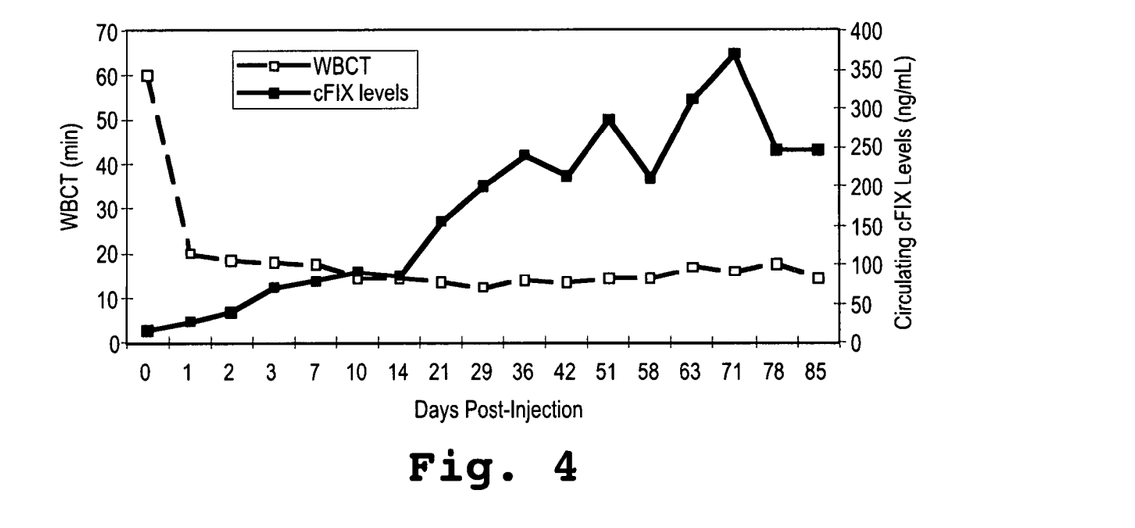
FIG. 4 is a graph showing whole blood clotting time (WBCT), in minutes, and plasma concentration of canine factor IX (cFIX) protein, in ng/mL, as a function of days post-injection into a dog suffering from hemophilia B of a vector containing a canine equivalent of the expression cassette identified as SEQ ID NO:6.

In a supporting study, a canine equivalent of the expression cassette of SEQ ID NO:6, and as shown in FIG. 3, was constructed. As described in Example 3, the vector was administered to a dog suffering from hemophilia B. Whole blood clotting time (WBCT) and circulating FIX levels were measured at several time points post injection, and the results are shown in FIG. 4. Clotting time was significantly reduced to normal levels within two days of the injection, and circulating FIX levels reached ~2% of normal within two weeks post-injection of the vector. There was no significant change in any physiological conditions tested by blood chemistries and complete blood counts. These results showed that the self-complementary vector was safe and effective.

Figure 5:
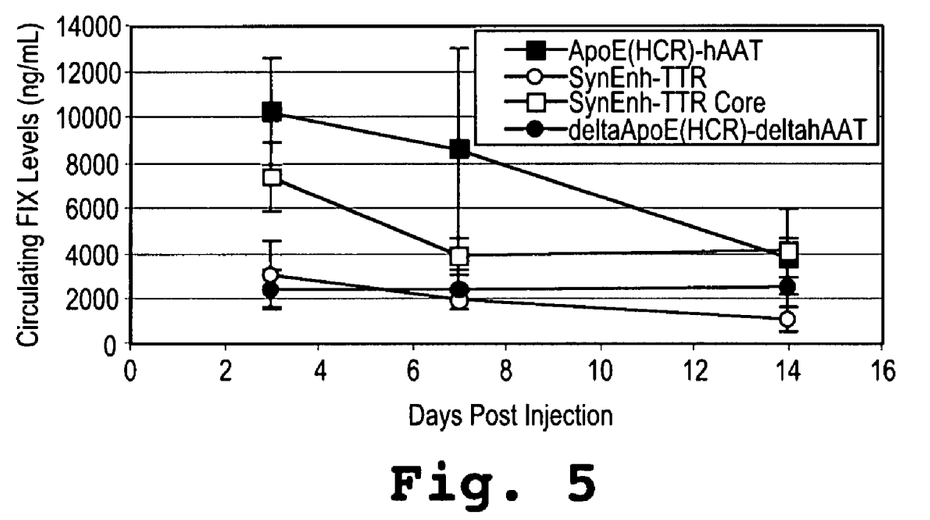
FIG. 5 is a graph showing the in vivo expression of hFIX in plasma, in ng/mL, after injection into mice of a plasmid containing a synthetic enhancer-TTR promoter of FIG. 1A (open circles), a synthetic enhancer-TTR core promoter of FIG. 1B (open squares), an ApoE(HCR) enhancer-hAAT promoter (filled squares), and a deltaApoE(HCR)-deltahAAT promoter (filled circles).

In another study, in vivo expression of human FIX for the enhancer/promoter combinations described herein were determined, and compared to the hFIX expression of an ApoE (HCR) enhancer-hAAT promoter and a deltaApoE(HCR)-deltahAAT promoter (Nathwani, A. C. et al., Blood, 107(7): 2653 (2005)). Following hydrodynamic tail vein injection of 20 µg of each plasmid into 3-5 mice per group, serum samples from each mouse were assayed for circulating FIX levels by ELISA experiments. As seen in FIG. 5, the Synthetic Enhancer (SynEnh) attached to the TTR-Core promoter (open squares) increased expression at day three by 2.5 fold, and is within the same statistical error of the ApoE(HCR)-hAAT enhancer/promoter (filled squares). Use of this improved enhancer/promoter in combination with the self-complimentary AAV genome, and the use of serotype AAV-8 vectors, is expected to give a total expression of FIX, or any other gene under its operative control, 5 to 15 fold higher than previous vectors. Thus, this improved gene expression and optimized efficacy of the vector provides a safe, effective, and long-term treatment for various conditions, such as hemophilia B.

II. Examples

The following examples are illustrative in nature and are in no way intended to be limiting.

Example 1

In Vitro Transfection and Expression

The expression profile of the SynEnh-TTR promoter was evaluated as follows. Two different plasmids were constructed. The first plasmid was comprised of the TTR promoter alone, which controlled expression of the Renilla luciferase gene. The second plasmid was comprised of combined SynEnh-TTR promoter (SEQ ID NO:3) controlling the expression of the Renilla luciferase gene.

The plasmids were transiently transfected into HUH-7 (liver hepatoma) and HEK293 (embryonic kidney) cell lines in triplicate. As a transfection and expression control, pGL3-Control vector (Promega) was cotransfected along with the plasmids. The pGL3-control vector contains the Firefly luciferase gene under the control of a ubiquitous SV40 promoter and enhancer.

Following incubation at standard tissue culture conditions for 36 hours, the quantities of Renilla and Firefly luciferases were measured. Results are shown in Table 1.

Example 2

In Vivo Transfection and Expression

Plasmids (pNEB 193 derivatives) containing a 2.3 kb expression cassette with the human or canine FIX (SEQ ID NO: 4 and SEQ ID NO: 5, respectively) under the control of SynEnh-TTR (SEQ ID NO: 3) were prepared.

In addition, plasmids containing the human or canine FIX sequences (SEQ ID NO: 4 and SEQ ID NO: 5, respectively) under the control of the apolipoprotein E hepatic control region (ApoE-HCR) and the human α1-antitrypsin promoter (hAAT) were prepared.

Forty micrograms of each plasmid containing an expression cassette was introduced into C57/B6 mice via hydrodynamic tail vein injection (Nakai et al., *Molecular Therapy*, 7:101-111 (2003)), and serum samples from each mouse were assayed post-injection for circulating FIX levels by ELISA. About 30% of the mouse liver hepatocytes were transfected with the plasmids. Circulating FIX levels (micrograms/milliliter) were measured three days post-injection and the results are shown in FIG. 2, where open squares and triangles correspond to FIX plasma concentrations from expression cassettes comprising SynEnh-TTR constructs, while closed squares and triangles represent FIX plasma concentrations for expression cassettes comprising ApoE-HCR and the human α1-antitrypsin promoter (hAAT). Standard deviations are indicated by vertical bars.

Example 3

In Vivo Transfection and Expression of FIX for Treatment of Hemophilia B

A canine equivalent of the expression cassette of SEQ ID NO:6, and as shown in FIG. 3, was constructed.

A single canine suffering from hemophilia B was injected by IV infusion with a single dose of $2.0 \times 10^{12}$ μg/kg. Whole blood clotting time (WBCT) and circulating FIX levels were measured at several time points post injection. Results are shown in FIG. 4.

While a number of exemplary aspects and embodiments have been discussed above, those of skill in the art will recognize certain modifications, permutations, additions and sub-combinations thereof. It is therefore intended that the following appended claims and claims hereafter introduced are interpreted to include all such modifications, permutations, additions and sub-combinations as are within their true spirit and scope.

---

What is claimed is:

1. An expression cassette, comprising:
   a synthetic enhancer;
   a transthyretin promoter; and
   a nucleotide sequence operably under the control of the synthetic enhancer and the transthyretin promoter, wherein the synthetic enhancer and the transthyretin promoter comprise a sequence having at least 95% sequence identity over the entire length of SEQ ID NO:3.

2. The expression cassette of claim 1, wherein the nucleotide sequence operably under the control of the synthetic enhancer and the transthyretin promoter comprises a factor IX coding sequence.

3. The expression cassette of claim 2, wherein the nucleotide sequence operably under the control of the synthetic enhancer and the transthyretin promoter is SEQ ID NO: 4.

4. An AAV vector, comprising the expression cassette of claim 1.

5. The AAV vector of claim 4, wherein the expression cassette is part of a self complementary AAV vector plasmid.

6. The AAV vector of claim 5, wherein the nucleotide sequence operably under the control of the synthetic enhancer and the transthyretin promoter is SEQ ID NO: 4.

7. The AAV vector of claim 6, further comprising an AAV-2 capsid gene or an AAV-8 capsid gene.

8. The expression cassette of claim 1, wherein the sequence of the synthetic enhancer and the transthyretin promoter is SEQ ID NO:3.

9. The expression cassette of claim 1, wherein the synthetic enhancer and the transthyretin promoter consists of a sequence with at least 98% sequence identity over the entire length of SEQ ID NO:3.

* * * * *

UNITED STATES PATENT AND TRADEMARK OFFICE
CERTIFICATE OF CORRECTION

PATENT NO. : 8,129,510 B2  
APPLICATION NO. : 11/731198  
DATED : March 6, 2012  
INVENTOR(S) : Mark Kay et al.

It is certified that error appears in the above-identified patent and that said Letters Patent is hereby corrected as shown below:

In the Specification:

Column 1, line 18 thereof: delete

"STATEMENT REGARDING GOVERNMENT INTEREST

This work was supported in part by the National Institutes of Health (NIH) Grant number HL 64274. Accordingly, the United States government may have certain rights."

Signed and Sealed this
Tenth Day of May, 2016

Michelle K. Lee
*Director of the United States Patent and Trademark Office*

SEQUENCE LISTING

```
<160> NUMBER OF SEQ ID NOS: 10

<210> SEQ ID NO 1
<211> LENGTH: 207
<212> TYPE: DNA
<213> ORGANISM: Artificial Sequence
<220> FEATURE:
<223> OTHER INFORMATION: Synthetic Enhancer

<400> SEQUENCE: 1
ggatctgtca attcacgcga gttaataatt accagcgcgg gccaaataaa taatcgcgag      60
gggcaggtga cgtttgccca gcgcgcgctg gtaattatta acctcgcgaa tattgattcg     120
aggccgcgat tgccgcaatc gcgaggggca ggtgaccttt gcccagcgcg cgttcgcccc     180
gccccggacg gtatcgatgt cgagggg                                         207

<210> SEQ ID NO 2
<211> LENGTH: 329
<212> TYPE: DNA
<213> ORGANISM: Artificial Sequence
<220> FEATURE:
<223> OTHER INFORMATION: Transthyretin Promoter

<400> SEQUENCE: 2
cactgggagg atgttgagta agatggaaaa ctactgatga cccttgcaga gacagagtat      60
taggacatgt ttgaacaggg gccgggcgat cagcaggtag ctctagaggt accccagatc     120
tagtgtctgt ctgcacattt cgtagagcga gtgttccgat actctaatct ccctaggcaa     180
ggttcatatt tgtgtaggtt acttattctc cttttgttga ctaagtcaat aatcagaatc     240
agcaggtttg gagtcagctt ggcagggatc agcagcctgg gttggaagga gggggtataa     300 aagcccttc accaggagaa gcccagctg                                       329
```

<210> SEQ ID NO 3
<211> LENGTH: 541
<212> TYPE: DNA
<213> ORGANISM: Artificial Sequence
<220> FEATURE:
<223> OTHER INFORMATION: Synthetic

<400> SEQUENCE: 3

```
ggatctgtca attcacgcga gttaataatt accagcgcgg gccaaataaa taatcgcgag      60
gggcaggtga cgtttgccca gcgcgcgctg gtaattatta acctcgcgaa tattgattcg     120
aggccgcgat tgccgcaatc gcgaggggca ggtgaccttt gcccagcgcg cgttcgcccc     180
gccccggacg gtatcgatgt cgagggggat cccactggga ggatgttgag taagatggaa     240
aactactgat gacccttgca gagacagagt attaggacat gtttgaacag gggccgggcg     300
atcagcaggt agctctagag gtaccccaga tctagtgtct gtctgcacat ttcgtagagc     360
gagtgttccg atactctaat ctccctaggc aaggttcata tttgtgtagg ttacttattc     420
tccttttgtt gactaagtca ataatcagaa tcagcaggtt ggagtcagc ttggcaggga      480
tcagcagcct gggttggaag gaggggtat aaaagcccct tcaccaggag aagcccagct      540
g                                                                    541
```

<210> SEQ ID NO 4
<211> LENGTH: 1780
<212> TYPE: DNA
<213> ORGANISM: Artificial Sequence
<220> FEATURE:
<223> OTHER INFORMATION: Synthetic

<400> SEQUENCE: 4

```
atgcagcgcg tgaacatgat catggcagaa tcaccaggcc tcatcaccat ctgccttta      60
ggatatctac tcagtgctga atgtacaggt ttgtttcctt ttttaaaata cattgagtat     120
gcttgccttt tagatataga aatatctgat gctgtcttct tcactaaatt ttgattacat     180
gatttgacag caatattgaa gagtctaaca gccagcacgc aggttggtaa gtactgtggg     240
aacatcacag attttggctc catgccctaa agagaaattg gctttcagat tatttggatt     300
aaaaacaaag acttttctaa gagatgtaaa attttcatga tgttttcttt tttgctaaaa     360
ctaaagaatt attcttttac atttcagttt ttcttgatca tgaaaacgcc aacaaaattc     420
tgaatcggcc aaagaggtat aattcaggta aattggaaga gtttgttcaa gggaaccttg     480
agagagaatg tatggaagaa aagtgtagtt ttgaagaagc acgagaagtt tttgaaaaca     540
ctgaaagaac aactgaattt tggaagcagt atgttgatgg agatcagtgt gagtccaatc     600
catgtttaaa tggcggcagt tgcaaggatg acattaattc ctatgaatgt tggtgtccct     660
ttggatttga aggaaagaac tgtgaattag atgtaacatg taacattaag aatggcagat     720
gcgagcagtt ttgtaaaaat agtgctgata caaggtggt tgctcctgt actgagggat     780
atcgacttgc agaaaccag aagtcctgtg aaccagcagt gccatttcca tgtggaagag     840
tttctgtttc acaaacttct aagctcaccc gtgctgaggc tgttttcct gatgtggact     900
atgtaaattc tactgaagct gaaaccattt tggataacat cactcaaagc acccaatcat     960
ttaatgactt cacgcgtgtt gttggtggag aagatgccaa accaggtcaa ttcccttggc    1020
aggttgtttt gaatggtaaa gttgatgcat tctgtggagg ctctatcgtt aatgaaaaat    1080
ggattgtaac tgctgcccac tgtgttgaaa ctggtgttaa attacagtt gtcgccggcg    1140
aacataatat tgaggagaca gaacatacag agcaaaagcg aaatgtgatt cgaattattc    1200
```

| | |
|---|---|
| ctcaccacaa ctacaatgca gctattaata agtacaacca tgacattgcc cttctggaac | 1260 |
| tggacgaacc cttagtgcta acagctacg ttacacctat ttgcattgct gacaaggaat | 1320 |
| acacgaacat cttcctcaaa tttggatctg gctatgtaag tggctgggga agagtcttcc | 1380 |
| acaaagggag atcagcttta gttcttcagt accttagagt tccacttgtt gaccgagcca | 1440 |
| catgtcttcg atctacaaag ttcaccatct ataacaacat gttctgtgct ggcttccatg | 1500 |
| aaggaggtag agattcatgt caaggagata gtgggggacc ccatgttact gaagtggaag | 1560 |
| ggaccagttt cttaactgga attattagct ggggtgaaga gtgtgcaatg aaaggcaaat | 1620 |
| atggaatata taccaaggta tcccggtatg tcaactggat taaggaaaaa acaaagctca | 1680 |
| cttaattaag tctagagtcg acctagaact agtaataaag gatcctttat tttcattgga | 1740 |
| tccgtgtgtt ggttttttgt gtgcggccgc gtcgagtcga | 1780 |

<210> SEQ ID NO 5
<211> LENGTH: 1777
<212> TYPE: DNA
<213> ORGANISM: Artificial Sequence
<220> FEATURE:
<223> OTHER INFORMATION: Synthetic

<400> SEQUENCE: 5

| | |
|---|---|
| atgcagcgcg tgaacatgat catggcagaa tcaccaggcc tcatcaccat ctgcctttta | 60 |
| ggatatctac tcagtgctga atgtacaggt ttgtttcctt ttttaaaata cattgagtat | 120 |
| gcttgccttt tagatataga aatatctgat gctgtcttct tcactaaatt ttgattacat | 180 |
| gatttgacag caatattgaa gagtctaaca gccagcacgc aggttggtaa gactgtggga | 240 |
| acatcacaga ttttggctcc atgccctaaa gagaaattgg ctttcagatt atttggatta | 300 |
| aaaacaaaga cttcttaag agatgtaaaa ttttcatgat gttttctttt ttgctaaaac | 360 |
| taaagaatta ttcttttaca tttcagtttt tcttgatcgt gaaaatgcca ccaaaattct | 420 |
| gagtcggcca aagaggtata attcaggtaa actggaagag tttgttcgag ggaaccttga | 480 |
| gagagaatgt atagaagaaa agtgcagttt tgaagaagca cgggaagttt ttgaaaacac | 540 |
| tgaaaaaacc actgaatttt ggaagcaata tgttgatgga gatcaatgtg aatccaatcc | 600 |
| atgtttaaat gacggtgtat gcaaggatga cattaattcc tatgaatgtt ggtgtcgagc | 660 |
| tggatttgaa ggaaagaact gtgaattaga tgtaacatgc aacattaaga atggcagatg | 720 |
| caagcagttt tgtaaattgg gccccgataa caaggtggtt tgttcctgta ctacgggata | 780 |
| ccaacttgcg gaagaccaaa ggtcctgtga accagcagtg ccatttccat gtggaagagt | 840 |
| ttctgtccct cacatttcta tgacacgcac ccgtgctgaa actctttttt ccaatatgga | 900 |
| ctatgaaaat tcaactgaag tggaaaaaat tttggataac gtcacccaac cgcttaacga | 960 |
| cttcactcga gttgttggtg gaaaagatgc caaaccaggt caatttcctt ggcaggtcct | 1020 |
| tttgaatggg aaagttgatg cattctgcgg aggttccatc atcaatgaaa atgggtggt | 1080 |
| aactgcagcc cactgtattg agcctgatgt taaaattacc atagttgcag gtgagcataa | 1140 |
| caccgagaag agggaacata cagagcagaa gcgaaacgtg attcgcacta ttcttccacca | 1200 |
| cagctataat gcaactatta ataagtacaa ccatgacatc gcccttctgg aactggatga | 1260 |
| gcccttaacg ctgaacagct atgtaacacc tatttgcatt gctgacaggg aatactcgaa | 1320 |
| catcttcctc aaatttgggt ctggctatgt gagtggctgg gggagagtct tcaacaaagg | 1380 |
| gcgatcggct tcaattcttc aatacttaa agttccactt gttgaccgag ccacgtgcct | 1440 |
| tcggtccacg aagttcacca tttataacaa catgttctgt gctggcttcc atgagggagg | 1500 |

| | |
|---|---:|
| taaagattca tgccagggcg atagtggggg accccatgtc accgaagtag aaggcataag | 1560 |
| tttcttaact gggattatta gctggggtga agagtgtgcg atgaaaggga agtatggaat | 1620 |
| atataccaag gtgtcccggt atgtcaactg gattaaagaa aagacgaagc tcacctaatt | 1680 |
| aattaagtct agagtcgacc tagaactagt aataaaggat cctttatttt cattggatcc | 1740 |
| gtgtgttggt tttttgtgtg cggccgcgtc gagtcga | 1777 |

<210> SEQ ID NO 6
<211> LENGTH: 1974
<212> TYPE: DNA
<213> ORGANISM: Artificial Sequence
<220> FEATURE:
<223> OTHER INFORMATION: Synthetic expression cassette

<400> SEQUENCE: 6

| | |
|---|---:|
| gagttaataa ttaccagcgc gggccaaata aataatccgc gaggggcagg tgacgtttgc | 60 |
| ccagcgcgcg ctggtaatta ttaacctcgc gaatattgat tcgaggccgc gattgccgca | 120 |
| atcgcgaggg gcaggtgacc tttgcccagc gggtacccgg gggcgcgcca gtgtctgtct | 180 |
| gcacatttcg tagagcgagt gttccgatac tctaatctcc ctaggcaagg ttcatatttg | 240 |
| tgtaggttac ttattctcct tttgttgact aagtcaataa tcagaatcag caggtttgga | 300 |
| gtcagcttgg cagggatcag cagcctgggt tggaaggagg gggtataaaa gcccctttcac | 360 |
| caggagaagc ccagctgggc gcgccggatc cttaattaaa tgcagcgcgt gaacatgatc | 420 |
| atggcagaat caccaggcct catcaccatc tgccttttag gatatctact cagtgctgaa | 480 |
| tgtacaggtt tgtttcatta aaaacaaaga ctttcttaag agatgtaaaa ttttcatgat | 540 |
| gttttctttt tgctaaaac taagaattta ttcttttaca tttcagtttt tcttgatcat | 600 |
| gaaaacgcca acaaaattct gaatcggcca aagaggtata attcaggtaa attggaagag | 660 |
| tttgttcaag ggaaccttga gagagaatgt atggaagaaa agtgtagttt tgaagaagca | 720 |
| cgagaagttt ttgaaaacac tgaaagaaca actgaatttt ggaagcagta tgttgatgga | 780 |
| gatcagtgtg agtccaatcc atgtttaaat ggcggcagtt gcaaggatga cattaattcc | 840 |
| tatgaatgtt ggtgtccctt tggatttgaa ggaaagaact gtgaattaga tgtaacatgt | 900 |
| aacattaaga atggcagatg cgagcagttt tgtaaaaata gtgctgataa caaggtggtt | 960 |
| tgctcctgta ctgagggata tcgacttgca gaaaaccaga agtcctgtga accagcagtg | 1020 |
| ccatttccat gtggaagagt ttctgttttca caaacttcta agctcacccg tgctgaggct | 1080 |
| gttttttcctg atgtggacta tgtaaattct actgaagctg aaaccatttt ggataacatc | 1140 |
| actcaaagca cccaatcatt taatgacttc acgcgtgttg ttggtggaga agatgccaaa | 1200 |
| ccaggtcaat tcccttggca ggttgttttg aatggtaaag ttgatgcatt ctgtggaggc | 1260 |
| tctatcgtta tgaaaaatg gattgtaact gctgccact gtgttgaaac tggtgttaaa | 1320 |
| attacagttg tcgccggcga acataatatt gaggagacag aacatacaga gcaaaagcga | 1380 |
| aatgtgattc gaattattcc tcaccacaac tacaatgcag ctattaataa gtacaaccat | 1440 |
| gacattgccc ttctggaact ggacgaaccc ttagtgctaa acagctacgt tacacctatt | 1500 |
| tgcattgctg acaaggaata cacgaacatc ttcctcaaat ttggatctgg ctatgtaagt | 1560 |
| ggctggggaa gagtcttcca caagggaga tcagctttag ttcttcagta ccttagagtt | 1620 |
| ccacttgttg accgagccac atgtcttcga tctacaaagt tcaccatcta taacaacatg | 1680 |
| ttctgtgctg gcttccatga aggaggtaga gattcatgtc aaggagatag tggggaccc | 1740 |
| catgttactg aagtggaagg gaccagtttc ttaactggaa ttattagctg gggtgaagag | 1800 |

```
tgtgcaatga aaggcaaata tggaatatat accaaggtat cccggtatgt caactggatt      1860
aaggaaaaaa caaagctcac ttaattaagt ctagagtcga cctagaacta gtaataaagg      1920
atcctttatt ttcattggat ccgtgtgttg gttttttgtg tgcggccgcg tcga            1974

<210> SEQ ID NO 7
<211> LENGTH: 377
<212> TYPE: DNA
<213> ORGANISM: Artificial Sequence
<220> FEATURE:
<223> OTHER INFORMATION: Synthetic enhancer/promoter

<400> SEQUENCE: 7
gagttaataa ttaccagcgc gggccaaata aataatccgc gaggggcagg tgacgtttgc        60
ccagcgcgcg ctggtaatta ttaacctcgc gaatattgat tcgaggccgc gattgccgca       120
atcgcgaggg gcaggtgacc tttgcccagc gggtacccgg gggcgcgcca gtgtctgtct       180
gcacatttcg tagagcgagt gttccgatac tctaatctcc ctaggcaagg ttcatatttg       240
tgtaggttac ttattctcct tttgttgact aagtcaataa tcagaatcag caggtttgga       300
gtcagcttgg cagggatcag cagcctgggt tggaaggagg gggtataaaa gccccttcac       360
caggagaagc ccagctg                                                     377

<210> SEQ ID NO 8
<211> LENGTH: 99
<212> TYPE: DNA
<213> ORGANISM: Homo sapiens

<400> SEQUENCE: 8
ggtttgtttc attaaaaaca aagactttct taagagatgt aaaattttca tgatgttttc        60 tttttttgcta aaactaaaga attattcttt tacatttca                             99

<210> SEQ ID NO 9
<211> LENGTH: 1485
<212> TYPE: DNA
<213> ORGANISM: Homo sapiens

<400> SEQUENCE: 9
atgcagcgcg tgaacatgat catggcagaa tcaccaggcc tcatcaccat ctgccttta         60 ggatatctac tcagtgctga atgtacaggt ttgtttcatt aaaaacaaag actttcttaa       120
gagatgtaaa attttcatga tgttttcttt tttgctaaaa ctaaagaatt attcttttac       180
atttcagttt ttcttgatca tgaaaacgcc aacaaaattc tgaatcggcc aaagaggtat       240
aattcaggta aattggaaga gtttgttcaa gggaaccttg agagagaatg tatggaagaa       300
aagtgtagtt ttgaagaagc acgagaagtt tttgaaaaca ctgaaagaac aactgaattt       360
tggaagcagt atgttgatgg agatcagtgt gagtccaatc catgtttaaa tggcggcagt       420
tgcaaggatg acattaattc ctatgaatgt tggtgtccct ttggatttga aggaaagaac       480
tgtgaattag atgtaacatg taacattaag aatggcagat gcgagcagtt ttgtaaaaat       540
agtgctgata caaggtggt tgctcctgt actgagggat atcgacttgc agaaaaccag       600
aagtcctgtg aaccagcagt gccatttcca tgtggaagag tttctgtttc acaaacttct       660
aagctcaccc gtgctgaggc tgttttttcct gatgtggact atgtaaattc tactgaagct       720
gaaaccattt tggataacat cactcaaagc acccaatcat ttaatgactt cacgcgtgtt       780
gttggtggag aagatgccaa accaggtcaa ttcccttggc aggttgtttt gaatggtaaa       840
gttgatgcat tctgtggagg ctctatcgtt aatgaaaaat ggattgtaac tgctgcccac       900
```

```
tgtgttgaaa ctggtgttaa aattacagtt gtcgccggcg aacataatat tgaggagaca        960
gaacatacag agcaaaagcg aaatgtgatt cgaattattc ctcaccacaa ctacaatgca       1020
gctattaata agtacaacca tgacattgcc cttctggaac tggacgaacc cttagtgcta       1080
aacagctacg ttacacctat ttgcattgct gacaaggaat acacgaacat cttcctcaaa       1140
tttggatctg gctatgtaag tggctgggga agagtcttcc acaaagggag atcagcttta       1200
gttcttcagt accttagagt tccacttgtt gaccgagcca catgtcttcg atctacaaag       1260
ttcaccatct ataacaacat gttctgtgct ggcttccatg aaggaggtag agattcatgt       1320
caaggagata gtgggggacc ccatgttact gaagtggaag ggaccagttt cttaactgga       1380
attattagct ggggtgaaga gtgtgcaatg aaaggcaaat atggaatata taccaaggta       1440
tcccggtatg tcaactggat taaggaaaaa acaaagctca cttaa                      1485

<210> SEQ ID NO 10
<211> LENGTH: 73
<212> TYPE: DNA
<213> ORGANISM: Artificial Sequence
<220> FEATURE:
<223> OTHER INFORMATION: Synthetic polyadenylation signal

<400> SEQUENCE: 10
ctagaactag taataaagga tcctttattt tcattggatc cgtgtgttgg ttttttgtgt         60
gcggccgcgt cga                                                           73
```